United States Patent
Cadena et al.

(10) Patent No.: US 6,906,128 B2
(45) Date of Patent: Jun. 14, 2005

(54) METHOD FOR DEPOSITING A POLYMER ONTO A SURFACE BY APPLYING A COMPOSITION ONTO SAID SURFACE

(75) Inventors: Natalie Cadena, Union City, NJ (US); Mathias Destarac, Paris (FR); Pascal Herve, West Windsor, NJ (US); Agnieszka Zofia Wilczewska, Bialystok (PL)

(73) Assignee: Rhodia Chimie, Boulogne Billancourt (FR)

( * ) Notice: Subject to any disclaimer, the term of this patent is extended or adjusted under 35 U.S.C. 154(b) by 0 days.

(21) Appl. No.: 10/317,625

(22) Filed: Dec. 12, 2002

(65) Prior Publication Data

US 2004/0010074 A1 Jan. 15, 2004

Related U.S. Application Data

(60) Provisional application No. 60/340,374, filed on Dec. 12, 2001.

(51) Int. Cl.$^7$ ............................................. C08F 220/02
(52) U.S. Cl. ........................... 524/522; 525/90; 525/94; 524/556; 524/555; 524/560; 424/47; 424/70.16; 424/70.22; 424/70.27
(58) Field of Search .................. 525/90, 94; 524/522, 524/556, 555, 560; 424/47, 70.16, 70.22, 70.27

(56) References Cited

U.S. PATENT DOCUMENTS

| | | | |
|---|---|---|---|
| 3,776,983 A | 12/1973 | Iovine | 260/901 |
| 5,273,676 A | 12/1993 | Boeckh | 252/174 |
| 5,362,485 A * | 11/1994 | Hayama et al. | 424/70.2 |
| 5,484,851 A | 1/1996 | Fock | 525/333 |
| 5,911,979 A * | 6/1999 | Midha et al. | 424/70.12 |
| 6,074,628 A * | 6/2000 | Bolich et al. | 424/47 |
| 6,093,410 A * | 7/2000 | Peffly et al. | 424/401 |
| 6,113,883 A * | 9/2000 | Midha et al. | 424/47 |
| 6,139,826 A | 10/2000 | Schraer | 424/70 |
| 6,235,813 B1 | 5/2001 | Brandt | 523/436 |
| 6,410,005 B1 * | 6/2002 | Galleguillos et al. | 424/70.16 |
| 6,451,747 B1 * | 9/2002 | Decoster | 510/119 |
| 6,589,517 B1 * | 7/2003 | McKelvey et al. | 424/70.1 |
| 6,663,855 B2 * | 12/2003 | Frechet et al. | 424/70.11 |

FOREIGN PATENT DOCUMENTS

| | | | |
|---|---|---|---|
| DE | 3131848 | 2/1983 | |
| WO | WO/0071591 | 11/2000 | |
| WO | WO/00/71660 | 11/2000 | |
| WO | WO 200071591 A1 * | 11/2000 | A01C/1/08 |

OTHER PUBLICATIONS

International Search Report of PCT/EP 02/14143.

* cited by examiner

*Primary Examiner*—Tatyana Zalukaeva
*Assistant Examiner*—Satya B Sastri

(57) ABSTRACT

The invention relates to a method for depositing a polymer onto a surface, by applying an aqueous composition, preferably an aqueous composition, onto said surface. The invention also relates to a method for making the composition. The composition comprise a block copolymer, comprising at least two blocks A and B, wherein block A is a polyionic block and block B is a neutral block.

14 Claims, No Drawings

METHOD FOR DEPOSITING A POLYMER ONTO A SURFACE BY APPLYING A COMPOSITION ONTO SAID SURFACE

CROSS REFERENCES TO RELATED APPLICATIONS

This application claims the priority under 35 U.S.C. 119 and/or 365 to Ser. No. 60/340,374 filed in the United States on Dec. 12, 2001.

BACKGROUND OF THE INVENTION

The invention relates to a method for depositing a polymer onto a surface, by applying an aqueous composition, preferably an aqueous composition, onto said surface. The invention also relates to a method for making the composition.

Depositing a polymer onto a surface is useful for various purposes. For example depositing a polymer may modify a surface tension, render a surface more or less hydrophilic or hydrophobic. Depositing a polymer may also modify the chemical properties of said surface to protect it or to render it compatible with another product. Another purpose may be to modify the surface aspect or touch, or to modify the mechanical properties of the product the polymer is deposited onto the surface. Depositing a polymer onto a surface may also be a mean for providing the surface, and the product the polymer is deposited onto, with an active compound. The polymer may modify the affinity of the surface for the active compound, and/or just be a carrier the compound is dispersed into.

Surfaces a polymer might be deposited onto may be hard surfaces to be cleaned, fabrics to be cleaned or treated to modify some of their properties, skin or hair.

For example, many compositions to be applied on hair, thereafter mentioned as hair-care compositions, such as shampoos, conditioners, volumizers, compositions combining several effects usually called "two in one", or more, comprise a polymer to be deposited onto the hair surface. In hair-care compositions, polymers are deposited for various purposes: modifying the mechanical properties of the hair, modifying its aspect, preventing entangling, easing combing and disentangling, helping the hair the remain in the shape it was dressed.

Examples of polymers comprised in hair-care compositions include polymers having a high molecular weight, cationic polymers, usually having high molecular weight. There is a need for extending the range of polymers to be deposited onto a surface, for example onto hair, in order to provide some new properties or functions, or to improve the performances, the cost and/or the environment impact of current compositions.

BRIEF SUMMARY OF THE INVENTION

Applicant has found that block copolymers comprising at least one polyionic block may be deposited onto a surface, for example onto hair or skin. Applicant has also found that applying a composition comprising said block copolymer could improve the deposition or the effect of some other compounds, preferably polymers, comprised in the composition.

Hence, a first aspect of the invention relates to a method for depositing a polymer onto a surface comprising the step of applying a composition comprising said polymer onto the surface, wherein the composition comprises a block copolymer (a), comprising at least two blocks A and B, wherein:

block A is a polyionic block in the pH conditions of the formulation, block B is a neutral block in the pH conditions of the formulation, and at least one block selected from the group consisting of block A and block B comprises units deriving from a mono-alpha-ethylenically-unsaturated monomer.

A second aspect of the invention relates to the use of the block copolymer as a deposition agent in a composition, or as a deposition aid agent in a composition.

A third aspect of the invention relates to compositions comprising the block copolymer, and optionally other compounds that will be mentioned below. In a preferred embodiment the compositions are hair-care or skin-care compositions, such as shampoos, hair-conditioners and the like.

DETAILED DESCRIPTION OF THE INVENTION

The method comprises applying a composition onto a surface. The composition comprises block copolymer (a), and may comprise some other compounds, such as a surfactant (b), and a polymer (c). It is mentioned that the deposition of the polymer might be obtained in a further step such as dilution, or another variation of the composition conditions.

The polymer being deposited is block polymer (a), optionally in the form of a complex with a surfactant (b). The polymer being deposited may also comprise another polymer (c), optionally in the form of a complex with block copolymer (a) and/or a surfactant (b).

The deposited polymer, either block polymer (a) alone or in a complex form with a surfactant, or a further polymer (c), optionally in a complex form with a surfactant and block copolymer (a), remains on the surface, at least partially, when it is rinsed with water, or with a aqueous solution comprising water. This is interesting in personal care applications, for example for making a two in one shampoo: a cleaning effect is provided by a surfactant while a conditioning effect is provided by a deposition of the polymer. Deposition occurs within a large scope of charge ratios Z, as defined below, typically of as low as 0.01 to as high as 100, for example of from 1 to 50.

Definitions

In the present specification, the molecular weight of a polymer, a copolymer, a moiety, a graft, a side-chain, a core, a branch, a block or a backbone refers to the weight-average molecular weight of said polymer, copolymer, moiety, graft, side-chain, core, branch, block or backbone. The weight-average molecular weight of the polymer or copolymer can be measured by gel permeation chromatography (GPC). In the present specification, the molecular weight of a graft, side-chain, core, branch, block or backbone refers to the molecular weight calculated from the amounts of monomers, polymers, initiators and/or transfer agents used to make the said graft, side-chain, core, branch, block or backbone. The one skilled in the art knows how to calculate these molecular weights. The ratios by weight between moieties refer to the ratios between the amounts of the compounds used to make said moieties, considering an extensive polymerization.

Typically, the molecular weight M of a block, graft, side-chain, branch, core or backbone is calculated according to the following formula:

$$M = \sum_i M_i * \frac{n_i}{n_{precursor}},$$

wherein $M_i$ is the molecular weight of a monomer i, $n_i$ is the number of moles of a monomer i, and $n_{precursor}$ is the number of moles of a compound the macromolecular chain of the block, graft, side-chain, branch, core or backbone will be linked to. Said compound may be a transfer agent or a transfer group, a previous block, or a graft or reactive side-chain. If it is a previous block, the number of moles may be considered as the number of moles of a compound the macromolecular chain of said previous block has been linked to, for example a transfer agent or a transfer group. It may be also obtained by a calculation from a measured value of the molecular weight of said previous block. If two blocks are simultaneously grown from a previous block, at both ends, the molecular weight calculated according to the above formula should be divided by two.

In the present specification, a unit deriving from a monomer is understood as a unit that may be directly obtained from the said monomer by polymerizing. Thus, a unit deriving from an ester of acrylic or methacrylic acid does not encompass a unit of formula —CH—CH(COOH)— or —CH—C(CH$_3$)(COOH)—, obtained for example by polymerizing an ester of acrylic or methacrylic acid and then hydrolyzing. But a unit deriving from acrylic acid or methacrylic acid encompasses for example a unit obtained by polymerizing a monomer and then reacting (for example hydrolyzing) to obtain units of formula —CH—CH(COOH)— or —CH—C(CH$_3$)(COOH)—.

In the present specification the charge ratio Z, is defined as the mole ratio between the amount of charges from optional surfactant (b) and the amount of charges resulting from the algebraic sum of charges from block copolymer (a) and optional polymer (c).

Thus, if surfactant (b) is anionic and block A is polycationic (optional polymer (a) being polycationic):

$$Z = \frac{\text{number of charges from compound }(b)}{\text{number of charges from polymer }(a) + \text{number of charges from copolymer }(c)}\left(\frac{(-)}{(+)}\right)$$

If surfactant (b) is cationic and block A is polyanionic (optional polymer (a) being polyanionic):

$$Z = \frac{\text{number of charges from compound }(b)}{\text{number of charges from polymer }(a) + \text{number of charges from copolymer }(c)}\left(\frac{(+)}{(-)}\right)$$

The composition may also comprise further ingredients. In the case other ingredients are also charged the definition of Z remains a charge ratio between compound (b) and same charge ingredients over the algebraic sum of charges carried by the polymer (a) and eventually copolymer (c) or same charge ingredients.

Details on preferred compositions are provided below.

Block Copolymer (a)

Block copolymer (a) comprises at least two different blocks, block A, and block B. It is preferably selected from the group consisting of (block A)–(block B) diblock copolymers, (block A)–(block B) triblock copolymers, and (block B)–(block A)–(block-B) triblock copolymers. The block copolymer is a linear block copolymer. By linear it is meant that the blocks arrangement is linear. However, a block may be a block having a comb polymer structure, that is comprising repetitive units comprising a polymeric moiety (macromonomers).

A block is usually defined by repeating units it comprises. A block may be defined by naming a polymer, or by naming monomers it is derived from. In the present specification, a unit deriving from a monomer is understood as a unit that may be directly obtained from the said monomer by polymerizing. Thus, a unit deriving from an ester of acrylic or methacrylic acid does not encompass a unit of formula —CH—CH(COOH)— or —CH—C(CH$_3$)(COOH)—, obtained for example by polymerizing an ester of acrylic or methacrylic acid and then hydrolyzing. But a unit deriving from acrylic acid or methacrylic acid encompasses for example a unit obtained by polymerizing a monomer and then reacting (for example hydrolyzing) to obtain units of formula —CH—CH(COOH)— or —CH—C(CH$_3$)(COOH)—.

A block may be a copolymer, comprising several kind of repeating units, deriving form several monomers. Hence, block A and block B are different polymers, deriving from different monomers, but they may comprise some common repeating units (copolymers). Block A and Block B preferably do not comprise more than 50% of a common repeating unit (derived from the same monomer).

Block A is a polyionic (polyanionic or polycationic) block in pH conditions of the formulation. That means that block A comprises ionic (anionic or cationic) repetitive units whatever the pH, or that block A comprises repetitive units that may be neutral or ionic (anionic or cationic) depending on the pH of the formulation (the units are potentially ionic). A unit that may be neutral or ionic (anionic or cationic), depending on the pH of the composition, will be thereafter referred to as an ionic unit (anionic or cationic), or as a unit deriving from an ionic monomer (anionic or cationic), whatever it is in a neutral form or in an ionic form (anionic or cationic).

In a particular embodiment of the invention, block A is a polycationic block, comprising units derived from cationic monomers.

Some preferred cationic monomers comprise an ammonium group of formula —NR$_3^+$, wherein R, which is identical or different, represents a hydrogen atom, an alkyl group comprising 1 to 10 carbon atoms, or a benzyl group, optionally carrying a hydroxyl group, and comprise an anion (counter-ion). Examples of anions are halides such as chloride and bromides, sulphates, hydrosulphates, alkylsulphates (for example comprising 1 to 6 carbon atoms), phosphates, citrates, formates, and acetates.

Examples of cationic monomers include
aminoalkyl (meth)acrylates, aminoalkyl (meth)acrylamides, monomers, including particularly (meth)acrylates, and (meth)acrylamides derivatives, comprising at least one secondary, tertiary or quaternary amine function, or a heterocyclic group containing a nitrogen atom, vinylamine or ethylenimine;
diallyldialkyl ammonium salts;
their mixtures, their salts, and macromonomers deriving from therefrom.

Examples of cationic monomers include:
dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide;
ethylenimine, vinylamine, 2-vinylpyridine, 4-vinylpyridine;
trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido (also called 2-(acryloxy)ethyltrimethylammonium, TMAEAMS) chloride, trimethylammonium ethyl (meth)acrylate (also called 2-(acryloxy)ethyltrimethylammonium, TMAEAMS) methyl sulphate, trimethyl ammonium propyl (meth)acrylamido chloride, vinylbenzyl trimethyl ammonium chloride, diallyidimethyl ammonium chloride,
monomers having the following formula:

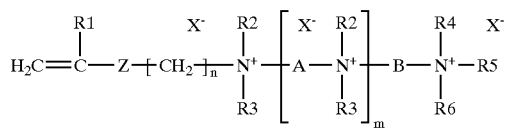

wherein

R₁ is a hydrogen atom or a methyl or ethyl group;

R₂, R₃, R₄, R₅ and R₆, which are identical or different, are linear or branched $C_1$–$C_6$, preferably $C_1$–$C_4$, alkyl, hydroxyalkyl or aminoalkyl groups;

m is an integer from 1 to 10, for example 1;

n is an integer from 1 to 6, preferably 2 to 4;

Z represents a —C(O)O— or —C(O)NH— group or an oxygen atom;

A represents a $(CH_2)_p$ group, p being an integer from 1 to 6, preferably from 2 to 4;

B represents a linear or branched $C_2$–$C_{12}$, advantageously $C_3$–$C_6$, polymethylene chain optionally interrupted by one or more heteroatoms or heterogroups, in particular O or NH, and optionally substituted by one or more hydroxyl or amino groups, preferably hydroxyl groups;

X, which are identical or different, represent counterions, and their mixtures, and macromonomers deriving therefrom.

In a particular embodiment of the invention, block A is a polyanionic block, comprising units deriving from anionic monomers.

Examples of anionic blocks are blocks comprising units deriving from anionic monomers selected from the group consisting of:

alpha-ethylenically-unsaturated monomers comprising a phosphate or phosphonate group, alpha-ethylenically-unsaturated monocarboxylic acids, monoalkylesters of alpha-ethylenically-unsaturated dicarboxylic acids, monoalkylamides of alpha-ethylenically-unsaturated dicarboxylic acids, alpha-ethylenically-unsaturated compounds comprising a sulphonic acid group, and salts of alpha-ethylenically-unsaturated compounds comprising a sulphonic acid group.

Preferred anionic blocks include blocks comprising deriving from at least one anionic monomer selected from the group consisting of:

acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulfonate (SS).

Block B is a neutral block in pH conditions of the formulation. Units comprised in block B are preferably neutral whatever the pH.

Examples of neutral blocks are blocks comprising units deriving from at least one monomer selected from the group consisting of:

alkyl oxides, such as ethylene oxide, and propylene oxide, acrylamide, methacrylamide, amides of alpha-ethylenically-unsaturated, preferably mono-alpha-ethylenically-unsaturated, monocarboxylic acids, esters of an alpha-ethylenically-unsaturated, preferably mono-alpha-ethylenically-unsaturated, monocarboxylic acid, for example alkyl esters such as such as methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, or hydroxyalkyl esters such as 2-hydroxyethylacrylate, polyethylene and/or polyporpylene oxide (meth)acrylates (i.e. polyethoxylated and/or polypropoxylated (meth) acrylic acid), vinyl alcohol, vinyl pyrrolidone, vinyl acetate, vinyl Versatate, vinyl nitriles, preferably comprising from 3 to 12 carbon atoms, acrylonitrile, vinylamine amides, vinyl aromatic compounds, such as styrene, and mixtures thereof.

Blocks that are ionic in the pH conditions of the formulation are usually considered as water-soluble. Thus, block A is usually considered as water-soluble. In a preferred embodiment of the invention, block B is water-soluble, or hydrophilic. Water-solubility of a block refers to the water-solubility that said block would have without the other block(s), that is the water-solubility of a polymer consisting of the same repeating units than said block, having the same molecular weight. By water-soluble block, polymer or copolymer, it is meant that the block, polymer or copolymer does not phase separate macroscopically in water at a concentration from 0.01% and 10% by weight, at a temperature from 20° C. to 30° C. By hydrophilic, it is meant that the moiety does not phase separate macroscopically in water at a concentration of from 0.1% and 1% by weight, at a temperature of from 20° C. to 30° C. By hydrophobic, it is meant that the moiety does phase separate macroscopically in water at a concentration of from 0.1% and 1% by weight, at a temperature of from 20° C. to 30° C.

Advantageously, block copolymer (a) is water-soluble, both block A and block B being hydrophilic and/or water-soluble.

As mentioned above, block B may be discriminated as regard to its hydrophilic or hydrophobic properties.

Examples of neutral blocks considered as hydrophilic include blocks comprising units deriving from at least one monomer selected from the group consisting of:

ethylene oxide, vinyl alcohol, vinyl pyrrolidone, acrylamide, methacrylamide, polyethylene oxide (meth)acrylate (i.e. polyethoxylated (meth)acrylic acid), hydroxyalkylesters of alpha-ethylenically-unsaturated, preferably mono-alpha-ethylenically-unsaturated, monocarboxylic acids, such as 2-hydroxyethylacrylate, and hdyroxyalkylamides of alpha-ethylenically-unsaturated, preferably mono-alpha-ethylenically-unsaturated, monocarboxylic acids.

Examples of neutral blocks considered as hydrophobic include blocks comprising units deriving from at least one monomer selected from the group consisting of:

propylene oxide, alkylesters of an alpha-ethylenically-unsaturated, preferably mono-alpha-ethylenically-unsaturated, monocarboxylic acid, such as methylacrylate, ethylacrylate, n-propylacrylate, n-butylacrylate, methylmethacrylate, ethylmethacrylate, n-propylmethacrylate, n-butylmethacrylate, and 2-ethyl-hexyl acrylate, acrylonitrile vinyl nitrites, comprising from 3 to 12 carbon atoms, vinylamine amides, and vinylaromatic compounds such as styrene.

At least one block selected from the group consisting of block A and block B derives from mono-alpha-ethylenically-unsaturated monomers. In a preferred embodiment, block A and block B derive from mono-alpha-ethylenically-unsaturated monomers. More precisely, it is meant that for block A and/or block B, at least 50% of the repeating units are mono-alpha-ethylenically-unsaturated monomers derived units.

From the monomers mentioned above, mono-alpha-ethylenically-unsaturated monomers include:

dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide;

ethylenimine, vinylamine, 2-vinylpyridine, 4-vinylpyridine;

trimethylammonium ethyl (meth)acrylate (also called 2-(acryloxy)ethyltrimethylammonium, TMAEAMS) chloride, trimethylammonium ethyl (meth)acrylate (also called 2-(acryloxy)ethyltrimethylammonium, TMAEAMS) methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, styrenesulfonate (SS), vinyl acetate, vinyl alcohol vinyl pyrrolidone styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, and 2-hydroxyethylacrylate.

There are several methods for making copolymer (c) comprising moieties A and B. In a particular embodiment, copolymer (c) is a block copolymer or a star copolymer. Some methods for making such copolymers are provided below.

It is possible for example to use anionic polymerization with sequential addition of 2 monomers as described for example by Schmolka, J. Am. Oil Chem. Soc. 1977, 54, 110; or alternatively Wilczek-Veraet et al., Macromolecules 1996, 29, 4036. Another method which can be used consists in initiating the polymerization of a block polymer at each of the ends of another block polymer as described for example by Katayose and Kataoka, Proc. Intern. Symp. Control. Rel. Bioact. Materials, 1996, 23, 899.

In the context of the present invention, it is recommended to use living or controlled polymerization as defined by Quirk and Lee (Polymer International 27, 359 (1992)). Indeed, this particular method makes it possible to prepare polymers with a narrow dispersity and in which the length and the composition of the blocks are controlled by the stoichiometry and the degree of conversion. In the context of this type of polymerization, there are more particularly recommended the copolymers which can be obtained by any so-called living or controlled polymerization method such as, for example:

free-radical polymerization controlled by xanthates according to the teaching of Application WO 98/58974 and U.S. Pat. No. 6,153,705, free-radical polymerization controlled by dithioesters according to the teaching of Application WO 98/01478, free-radical polymerization controlled by dithioesters according to the teaching of Application WO 99/35178, free-radical polymerization controlled by dithiocarbamates according to the teaching of Application WO 99/35177, free-polymerization using nitroxide precursors according to the teaching of Application WO 99/03894, free-radical polymerization controlled by dithiocarbamates according to the teaching of Application WO 99/31144, free-radical polymerization controlled by dithiocarbazates according to the teaching of Application WO 02/26836, free-radical polymerization controlled by halogenated Xanthates according to the teaching of Application WO 00/75207 and U.S. application Ser. No. 09/980,387, free-radical polymerization controlled by dithiophosphoroesters according to the teaching of Application WO 02/10223, free-radical polymerization controlled by a transfer agent in the presence of a disulphur compound according to the teaching of Application WO 02/22688, atom transfer radical polymerization (ATRP) according to the teaching of Application WO 96/30421, free-radical polymerization controlled by iniferters according to the teaching of Otu et al., Makromol. Chem. Rapid. Commun., 3, 127 (1982), free-radical polymerization controlled by degenerative transfer of iodine according to the teaching of Tatemoto et al., Jap. 50, 127, 991 (1975), Daikin Kogyo Co Ltd Japan, and Matyjaszewski et al., Macromolecules, 28, 2093 (1995), group transfer polymerization according to the teaching of Webster O. W., "Group Transfer Polymerization", p. 580–588, in the "Encyclopedia of Polymer Science and Engineering", Vol. 7, edited by H. F. Mark, N. M. Bikales, C. G. Overberger and G. Menges, Wiley Interscience, New York, 1987, radical polymerization controlled by tetraphenylethane derivatives (D. Braun et al., Macromol. Symp., 111, 63 (1996)), radical polymerization controlled by organocobalt complexes (Wayland et al., J. Am. Chem. Soc., 116, 7973 (1994)).

Preferred processes are sequenced living free-radical polymerization processes, involving the use of a transfer agent. Preferred transfer agents are agents comprising a group of formula —S—C(S)—Y—, —S—C(S)—S—, or —S—P(S)—Y—, or —S—P(S)—S—, wherein Y is an atom different from sulfur, such as an oxygen atom, a nitrogen atom, and a carbon atom. They include dithioester groups, thioether-thione groups, dithiocarbamate groups, dithiphosphoroesters, dithiocarbazates, and xanthate groups. Examples of groups comprised in preferred transfer agents include groups of formula —S—C(S)—NR—NR'$_2$, —S—C(S)—NR—N=CR'$_2$, —S—C(S)—O—R, —S—C(S)—CR=CR'$_2$, and —S—C(S)—X, wherein R and R' are or identical or different hydrogen atoms, or organic groups such as hydrocarbyl groups, optionally substituted, optionally comprising heteroatoms, and X is an halogen atom. A preferred polymerization process is a living radical polymerization using xanthates.

Copolymers obtained by a living or controlled free-radical polymerization process may comprise at least one transfer agent group at an end of the polymer chain. In particular embodiment such a group is removed or deactivated.

A "living" or "controlled" radical polymerization process used to make the block copolymers comprises the steps of:
a) reacting a mono-alpha-ethylenically-unsaturated monomer, at least a free radicals source compound, and a transfer agent, to obtain a first block, the transfer agent being bounded to said first block,
b1) reacting the first block, another mono-alpha-ethylenically-unsaturated monomer, and, optionally, at least a radical source compound, to obtain a di-block copolymer,
b2) optionally, repeating n times (n being equal to or greater than 0) step b1) to obtain a (n-2)-block copolymer, and then
c) optionally, reacting the transfer agent with means to render it inactive.

For example, a "living" or "controlled" radical polymerization process used to make the di-block copolymers comprises the steps of:
a) reacting a mono-alpha-ethylenically-unsaturated monomer, at least a free radicals source compound, and a transfer agent, to obtain a first block, the transfer agent being bounded to said first block,
b) reacting the first block, another mono-alpha-ethylenically-unsaturated monomer, and, optionally, at least a radical source compound, to obtain a di-block copolymer, and then
c) optionally, reacting the transfer agent with means to render it inactive.

During step a), a first block of the polymer is synthesized. During step b), b1), or b2), another block of the polymer is synthesized.

Star copolymers may be prepared also by a living or controlled polymerization process involving preparing first the core and then growing branches therefrom ("core first" embodiment), or preparing first the branches and then linking the branches with a core ("arm first" embodiment.

Examples of transfer agents are transfer agents of the following formula (I):

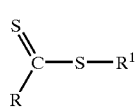

(I)

wherein:
R represents an R$^2$O—, R$^2$R'$^2$N— or R$^3$— group, R$^2$ and R'$^2$, which are identical or different, representing (i) an alkyl, acyl, aryl, alkene or alkyne group or (ii) an optionally aromatic, saturated or unsaturated carbonaceous ring or (iii) a saturated or unsaturated heterocycle, it being possible for these groups and rings (i), (ii) and (iii) to be substituted, R$^3$ representing H, Cl, an alkyl, aryl, alkene or alkyne group, an optionally substituted, saturated or unsaturated (hetero)cycle, an alkylthio, alkoxycarbonyl, aryloxycarbonyl, carboxyl, acyloxy, carbamoyl, cyano, dialkyl- or diarylphosphonato, or dialkyl- or diarylphosphinato group, or a polymer chain, R$^1$ represents (i) an optionally substituted alkyl, acyl, aryl, alkene or alkyne group or (ii) a carbonaceous ring which is saturated or unsaturated and which is optionally substituted or aromatic or (iii) an optionally substituted, saturated or unsaturated heterocycle or a polymer chain, and The R$^1$, R$^2$, R'$^2$ and R$^3$ groups can be substituted by substituted phenyl or alkyl groups, substituted aromatic groups or the following groups: oxo, alkoxycarbonyl or aryloxycarbonyl (—COOR), carboxyl (—COOH), acyloxy (—O$_2$CR), carbamoyl (—CONR$_2$), cyano (—CN), alkylcarbonyl, alkylarylcarbonyl, arylcarbonyl, arylalkylcarbonyl, isocyanato, phthalimido, maleimido, succinimido, amidino, guanidino, hydroxyl (—OH), amino (—NR$_2$), halogen, allyl, epoxy, alkoxy (—OR), S-alkyl, S-aryl or silyl, groups exhibiting a hydrophilic or ionic nature, such as alkaline salts of carboxylic acids or alkaline salts of sulphonic acid, poly(alkylene oxide) (PEO, PPO) chains, or cationic substituents (quaternary ammonium salts), R representing an alkyl or aryl group.

Preferably, the transfer agent of formula (I) is a dithiocarbonate chosen from the compounds of following formulae (IA), (IB) and (IC):

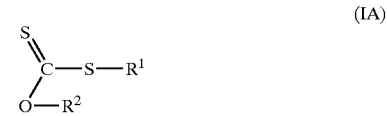

(IA)

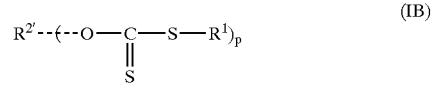

(IB)

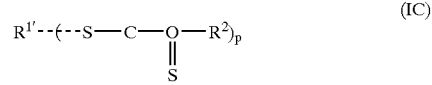

(IC)

wherein:
R$^2$ and R$^{2'}$ represent (i) an alkyl, acyl, aryl, alkene or alkyne group or (ii) an optionally aromatic, saturated or unsaturated carbonaceous ring or (iii) a saturated or unsaturated heterocycle, it being possible for these groups and rings (i), (ii) and (iii) to be substituted, R$^1$ and R$^{1'}$ represent (i) an optionally substituted alkyl, acyl, aryl, alkene or alkyne group or (ii) a carbonaceous ring which is saturated or unsaturated and which is optionally substituted or aromatic or (iii) an optionally substituted, saturated or unsaturated heterocycle or a polymer chain, and p is between 2 and 10.

Other examples of transfer agents are transfer agents of the following formulae (II) and (III):

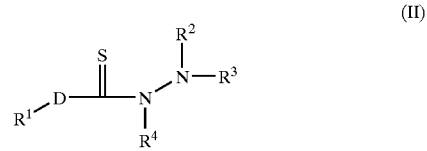

(II)

-continued

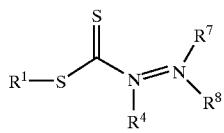

(III)

wherein
- $R^1$ is an organic group, for example a group $R^1$ as defined above for tranfer agents of formulae (I), (IA), (IB), and (IC),
- $R^2$, $R^3$, $R^4$, $R^7$, and $R_8$ which are identical or different are hydrogen atoms or organic groups, optionally forming rings. Examples of $R_2$, $R^3$, $R^4$, $R^7$, and $R^8$ organic groups include hydrocarbyls, subsituted hydrocabyls, heteroatom-containing hydrocarbyls, and substututed heteroatom-containing hydrocarbyls.

The mono-alpha-ethylenically-unsaturated monomers and their proportions are chosen in order to obtain the desire properties for the block(s). According to this process, if all the successive polymerizations are carried out in the same reactor, it is generally preferable for all the monomers used during one stage to have been consumed before the polymerization of the following stage begins, therefore before the new monomers are introduced. However, it may happen that monomers of the preceding stage are still present in the reactor during the polymerization of the following block. In this case, these monomers generally do not represent more than 5 mol % of all the monomers.

The polymerization can be carried out in an aqueous and/or organic solvent medium. The polymerization can also be carried out in a substantially neat melted form (bulk polymerization), or according to a latex type process in an aqueous medium.

The molecular weight of block copolymer (c) is preferably comprised between 1000 and 500000 g/mol. It is more preferably less than 100000 g/mol, and further more preferably between 15000 and 20000 g/mol. Within these ranges, the weight ratio of each block may vary. It is however preferred that each block have a molecular weight above 500 g/mol, and preferably above 1000 g/mol.

Surfactant (b)

In a particular embodiment of the invention, the composition further comprises a surfactant (b). Surfactant (b) is preferably an ionic (cationic or anionic) surfactant, in pH conditions of the composition.

In a preferred embodiment:
- if surfactant (b) is an anionic surfactant in the pH condition of the composition, then block A is a cationic block in the pH conditions of the composition (i.e. surfactant and block A have opposite charges), or
- if surfactant (b) is a cationic surfactant in the pH conditions of the composition, then block A is a polyanionic block in the pH conditions of the composition (i.e. surfactant and block A have opposite charges).

When surfactant (b) and block copolymer (a) have opposite charges, they usually form a complex, preferably dispersed in water in the composition. Said complex, comprising block copolymer (a) deposits onto the surface. In a preferred embodiment, the surface is skin or hair, the surfactant is an anionic surfactant in the pH conditions of the composition, block A is a polycationic block in the pH conditions of the composition, and block B is an hydrophilic water-soluble block. Z may be up to 50.

Examples of cationic surfactants (b) include the following compounds:
primary, secondary or tertiary mono- or polyamines, or those possessing one or more quaternary ammonium groups, more particularly comprising 6 to 40 carbon atoms linear or branched aliphatic, aromatic, as well as those optionally comprising one or more alcoxylated ethoxylated and/or propoxylated groups. There may be cited as examples, hexylamine, octylamine, dodecylamine, stearylamine, hexadecylamine, oleylamine, diaminohexane, diaminoheptane, diaminododecane, benzoctamine, alkyldialkylammonium or alkyltrialkylammonium or alkylbenzyldialkylammonium halides, such as chloride, dodecyltrimethyl-ammonium bromide, chloride, hexadecyltrimethylammonium bromide, chloride, benzalkonium bromide;
piperidinium salts,
imidazoles,
heterocyclic amines, and
mixture thereof.

It is to be noted that the scope of the present invention would not be exceeded by using, on their own or in a combination with the aforementioned surfactants, one or more amphoteric surfactants, which according to the temperature and pH conditions of the composition are in a cationic form, or can develop towards such a form. It is emphasized that an amphoteric surfactant carries an anionic charge and/or a cationic charge; its degree of ionisation varies according to the pH of the medium in which it is found.

As examples of such surfactants, there may be cited in particular betaines, such as in particular lauryl betaine (Mirataine BB from the company Rhodia Chimie); sulfobetaines: amidoalkylbetaines, such as cocoamidopropylbetaine (Mirataine BDJ from the company Rhodia Chimie); alkylampho-acetates or -diacetates, such as cocoamphoacetates and cocoamphodiacetates (Miranol C2M, Miranol Ultra C32 from the company Rhodia Chimie), alkylamphopropionates or -dipropionates, such as Miranol C2M SF of the Rhodia Chimie company, on their own or in a mixture.

Examples of anionic surfactants (b) include the following compounds:
alkyl ester sulphonates, alkylbenzene sulphonates, primary or secondary alkylsulphonates, alkylglycerol sulphonates, sulphonated polycarboxylic acids.
alkylsulphates, sulphates of alkylglycosides, sulphated alkyl amides,
alkylphosphates.
the salts of saturated or unsaturated fatty acids, paraffin sulphonates, N-acyl N-alkyltaurates, isethionates, alkylsuccinamates, N-acyl sarcosinates,
alkylsulfosuccinates, monoesters or diesters of sulfosuccinates,
polyethoxycarboxylates.

As more precise examples of such surfactants the following can be mentioned:
Alkylester sulphonates of formula R—CH($SO_3M$)—COOR', where R represents an alkyl radical in $C_8$–$C_{20}$, preferably in $C_{10}$–$C_{16}$, R' an alkyl radical in $C_1$–$C_6$, preferably in $C_1$–$C_3$ and M an alkaline cation (sodium, potassium, lithium), substituted or non-substituted ammonium (methyl-, dimethyl-, trimethyl-, tetramethylammonium, dimethylpiperidinium . . . ) or alcanolamine derivative (monoethanolamine, diethanolamine, triethanolamine . . . ). The methyl ester sulphonates, the R radical of which is in $C_{14}$–$C_{16}$, can quite particularly be mentioned:
the alkylsulphates of formula $ROSO_3M$, where R represents an alkyl or hydroxyalkyl radical in $C_5$–$C_{24}$, preferably in $C_{10}$–$C_{18}$, M representing a hydrogen atom or a cation with the same definition as above, as well as their ethoxylated (EO) and/or propoxylated (PO) derivatives, on average having from 0.5 to 30 units, preferably from 0.5 to 10 EO and/or PO units;

the sulphated alkylamides of formula RCONHR'OSO$_3$M where R represents an alkyl radical in C$_2$–C$_{22}$, preferably in C$_6$–C$_{20}$, R' an alkyl radical in C$_2$–C$_3$, M representing a hydrogen atom or a cation of the same definition as above, as well as their ethoxylated (EO) and/or propoxylated (PO) derivatives, having on average from 0.5 to 60 EO and/or PO units;

the salts of saturated or unsaturated fatty acids in C$_8$–C$_{24}$, preferably in C$_{14}$–C$_{20}$, alkylbenzenesulphonates in C$_9$–C$_{20}$, primary or secondary alkylsulphonates in C$_8$–C$_{22}$, alkylglycerol sulphonates, sulphonated polycarboxylic acids, paraffin sulphonates, N-acyl N-alkyltaurates, alkylphosphates, isethionates, alkylsuccinamates, alkylsulfosuccinates, the monoesters or diesters, of N-acyl sulfosuccinate sarcosinates, the sulphates of alkylglycosides, polyethoxycarboxylates; the cation being an alkali metal (sodium, potassium, lithium), a substituted or non-substituted ammonium residue (methyl-, dimethyl-, trimethyl-, tetramethylammonium, dimethylpiperidinium . . . ) or alcanolamine derivative (monoethanolamine, diethanolamine, triethanolamine . . . ).

It is to be noted that the scope of the present invention would not be exceeded by using, on their own or combined with the aforementioned surfactants, amphoteric surfactants which depending on the temperature and pH conditions of the composition are in an anionic form, or can develop into such a form. Some aforementioned amphoteric surfactants may be suitable for this embodiment, such as for example betaines, amidoalkylbetaines; alkylamphoacetates and alkylamphodiacetates; alkylamphopropionates or alkyl amphodipropionates, on their own or in a mixture.

Polymer (c)

In a particular embodiment of the invention, the composition further comprises a polyionic polymer (c), that interacts with the surface. It is mentioned that polyorganosiloxanes (silicones) are not encompassed by polymer (c).

In a particular embodiment, advantageous, block A and polymer (c) are alike, meaning that at least 25%, preferably 50%, of the repetitive units comprised therein are identical. They preferably essentially consist of the same units. However, their molecular weight may be different.

In a preferred embodiment:
  polymer (c) is a polycationic polymer in the pH condition of the composition, if block A is a polycationic block in the pH conditions of the composition, or
  polymer (c) is a polyanionic polymer in the pH conditions of the composition, if block A is a polyanionic block in the pH conditions of the composition.

In an even more preferred embodiment, the composition comprises surfactant (b) and polymer (c), and:
  surfactant (b) is an anionic surfactant in the pH condition of the composition, and polymer (c) is a polycationic polymer in the pH condition of the composition, if block A is a polycationic block in the pH conditions of the composition, or
  surfactant (b) is a cationic surfactant in the pH conditions of the composition, and polymer (c) is a polyanionic polymer in the pH condition of the composition if block A is a polyanionic block in the pH conditions of the composition.

According to this embodiment, the surface is preferably skin surface or hair surface, surfactant (b) is an anionic surfactant in the pH condition of the composition, polymer (c) is a polycationic polymer in the pH condition of the composition, and block A is a polycationic block in the pH conditions of the composition.

Block copolymer (a), surfactant (b), and polymer (c) may form a complex. For example, a surfactant (b) being anionic in the pH condition of the composition, a polymer (c) being polycationic in the pH condition of the composition, and a block copolymer (a) wherein block A is a polycationic block in the pH conditions of the composition, may form a complex. Said complex, comprising block copolymer (a), deposits onto the surface.

Examples of polycationic polymer (c) include hydroxyalkylated (C$_2$–C$_{22}$) derivatives of cationic guars such as hydroxypropyl guar hydroxypropyl trimonium chloride (JAGUAR C162 and JAGUAR C2000 sold by Rhodia) and cationic cellulose derivatives, in particular cellulose,2-(2-hydroxy-3-(trimethylammonium)propoxy)ethyl ether, chloride or polyquaternium-10 (polymer JR400 sold by Union Carbide). The cationic nature of these polymers is variable: thus in the case of cationic hydroxypropylated guar derivatives such as JAGUAR C162 and C2000 sold by Rhodia, the degree of hydroxypropylation (molar substitution, MS), is in the range 0.02 to 1.2 and the degree of substitution, DS is in the range 0.01 to 0.6. These products can optionally be functionalised by hydrophobic groups such as alkyl chains. These cationic polymers can optionally be functionalised by anionic groups such as carboxymethyl, sulphate, sulphonate or phosphate, provided that the degree of substitution of these anionic groups is always less than the degree of substitution of the cationic groups. The molecular weight of these cationic polymers is generally at least 2000, more generally of the order of 200000 to 3000000.

Examples of cationic polymers (c) also include polymers comprising units deriving from monomers selected from the group consisting of:

dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide;

ethylenimine, vinylamine, 2-vinylpyridine, 4-vinylpyridine;

trimethylammonium ethyl (meth)acrylate (also called 2-(acryloxy)ethyltrimethylammonium, TMAEAMS) chloride, trimethylammonium ethyl (meth)acrylate (also called 2-(acryloxy)ethyltrimethylammonium, TMAEAMS) methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, monomers having the following formula:

$$H_2C=\overset{R_1}{\underset{}{C}}-Z\text{---}(CH_2)_n\text{---}\overset{R_2}{\underset{R_3}{N^+}}\text{---}X^-\left[\text{---}A\text{---}\overset{R_2}{\underset{R_3}{N^+}}\text{---}X^-\right]_m\text{---}B\text{---}\overset{R_4}{\underset{R_6}{N^+}}\text{---}R_5\quad X^-$$

wherein

R$_1$ is a hydrogen atom or a methyl or ethyl group;

R$_2$, R$_3$, R$_4$, R$_5$ and R$_6$, which are identical or different, are linear or branched C$_1$–C$_6$, preferably C$_1$–C$_4$, alkyl, hydroxyalkyl or aminoalkyl groups;

m is an integer from 1 to 10, for example 1;

n is an integer from 1 to 6, preferably 2 to 4;

Z represents a —C(O)O— or —C(O)NH— group or an oxygen atom;

A represents a (CH$_2$)$_p$ group, p being an integer from 1 to 6, preferably from 2 to 4;

B represents a linear or branched C$_2$–C$_{12}$, advantageously C$_3$–C$_6$, polymethylene chain optionally interrupted by one or more heteroatoms or heterogroups, in particular O or NH, and optionally substituted by one or more hydroxyl or amino groups, preferably hydroxyl groups;

X, which are identical or different, represent counterions, and their mixtures, and macromonomers deriving therefrom.

Examples of anionic polymers (c) include polymers comprising units deriving from monomers selected from the group consisting of:

alpha-ethylenically-unsaturated monocarboxylic acids, such as acrylic acid and methacrylic acid, monoalkylesters of alpha-ethylenically-unsaturated dicarboxylic acids, preferably monoalkylesters of mono-alpha-ethylenically-unsaturated dicarboxylic acids, monoalkylamides of alpha-ethylenically-unsaturated dicarboxylic acids, preferably monoalkylamides of mono-alpha-ethylenically unsaturated dicarboxylic acids, alpha-ethylenically-unsaturated, preferably mono-alpha-ethylenically-unsaturated, compounds comprising a sulfonic acid group, and salts thereof, such as:

vinyl sulfonic acid, salts of vinyl sulfonic acid, vinylbenzene sulfonic acid, salts of vinylbenzene sulfonic acid, alpha-acrylamidomethylpropanesulfonic acid, salts of alpha-acrylamidomethylpropanesulfonic acid 2-sulfoethyl methacrylate, salts of 2-sulfoethyl methacrylate, acrylamido-2-methylpropanesulfonic acid (AMPS), salts of acrylamido-2-methylpropanesulfonic acid, styrenesulphonate (SS), alpha-ethylenically-unsaturated monomers comprising a phosphate or phosphonate group, and salts thereof, and their mixtures, their salts, and macromonomers deriving from therefrom.

Further Compounds

The compositions may comprise further compounds. The composition preferably comprises water, and is preferably an aqueous solution, dispersion, suspension (for example a colloidal suspension of complexes) or emulsion, of block copolymer (a) and/or surfactant (b) and/or polymer (c) and/or further compounds.

The composition may comprise insoluble organic compounds which can be present in the form of particles which can also be mentioned include oils which can exert conditioning, protective or emollient functions; the oils are generally selected from alkylmonoglycerides, alkyldiglycerides, triglycerides such as oils extracted from plants and vegetables (palm oil, coprah oil, cottonseed oil, soyabean oil, sunflower seed oil, olive oil, grapeseed oil, sesame seed oil, peanut oil, castor oil . . . ) or oils of animal origin (tallow, fish oils . . . ), derivatives of these oils such as hydrogenated oils, lanolin derivatives, mineral oils or paraffin oils, perhydrosqualane, squalene, diols such as 1,2-dodecanediol, cetyl alcohol, stearyl alcohol, oleic alcohol, fatty esters such as isopropyl palmitate, 2-ethylhexyl cocoate, myristyl myristate, or lactic acid esters of stearic acid, behenic acid, isostearic acid.

The composition may comprise Bactericidal or fungicidal agents to improve skin disinfection can also be mentioned, such as triclosan, anti-dandruff agents such as zinc pyrithone or octopyrox, or insecticidal agents such as natural or synthetic pyrethroids. These different organic molecules can if necessary be previously encapsulated in appropriate matrices using methods which are known in the art. An example which can be cited is encapsulation of organic molecules in polymer latexes.

The composition may comprise water-insoluble organic particles, which can also be constituted by agents for protecting the skin and/or hair against sun damage and UV damage, such as solar filters which are chemical compounds which strongly absorb UV radiation such as the compounds authorised in European Directive 76/768/EEC, its annexes and subsequent amendments.

In a particular embodiment, the composition is a cosmetic composition. Such a composition can be formulated into a large number of types of products for the skin and/or hair, gels (in particular styling gels), conditioners, formulations for styling or to facilitate combing the hair, rinsing formulae, body and hand lotions, products regulating skin hydration, toilet milks, make-up remover, shampoos, shower gels, liquid soaps and other compositions of similar type.

A cosmetic composition may comprise moistening agents into the cosmetic compositions of the invention, such as glycerol, sorbitol, urea, collagen, gelatin, aloe vera or hyaluronic acid.

In order to further reduce irritation or damage to the scalp, it is also possible to add hydrosoluble or hydrodispersible polymers such as collagen or certain non allergenic derivatives of animal or vegetable proteins (wheat protein hydrolysates, for example), natural hydrocolloids (guar gum, carouba gum, tara gum . . . ) or from fermentation processes, and derivatives of these polycarbohydrates such as modified celluloses (for example hydroxyethylcellulose, carboxymethylcellulose), guar derivatives or carouba derivatives such as their non ionic derivatives (for example hydroxypropylguar), anionic derivatives (carboxymethylguar and carboxymethylhydroxypropylguar).

Preservatives such as methyl, ethyl, propyl and butyl esters of p-hydroxybenzoic acid, sodium benzoate, GERMABEN (trade name) or any chemical agent preventing bacterial or mould proliferation and traditionally used in cosmetic compositions are generally introduced into these compositions in an amount of 0.01% to 3% by weight. The quantity of these products is generally adjusted to avoid any proliferation of bacteria, mould or yeasts in the cosmetic compositions.

As an alternative to chemical agents, sometimes agents which modify the activity of water by greatly increasing the osmotic pressure can be used, such as carbohydrates or salts, can be used.

In general, in order to increase the pleasurable feel when the composition is used by the consumer, these ingredients have added to them one or more fragrances, colouring agents including those described in annex IV ("List of colouring agents allowed for use in cosmetic products") of European Directive 76/768/EEC dated 27 Jul. 1976, the Cosmetics Directive, and/or opacifying agents such as pigments. Fragrances, colouring agents or pigments can be added.

The composition can also contain viscosifying agents or gelling agents, such as cross-linked polyacrylates—CARBOPOL sold by GOODRICH, cellulose derivatives such as hydroxypropylcellulose, carboxymethylcellulose, guars and their derivatives, etc., used alone or in combination, or the same compounds, generally in the form of hydrosoluble polymers modified by hydrophobic groups covalently bonded to the polymer skeleton as described in International patent application WO-A-92/16187 and/or water to bring the total of the constituents of the formulation to 100%.

Cosmetic compositions of the invention can also contain polymeric dispersing agents in a quantity of the order of 0.1% to 7% by weight, to control the calcium and magnesium hardness, such as:

hydrosoluble salts of polycarboxylic acids with a molecular mass of the order of 2000 to 100000, obtained by polymerisation or copolymerisation of ethylenically unsaturated carboxylic acids such as acrylic acid, maleic acid or anhydride, fumaric acid, itaconic acid, aconitic acid, mesaconic acid, citraconic acid, methylenemalonic acid, and more particularly polyacrylates with a molecular mass of the order of 2000 to 10000 (U.S. Pat. No. 3,308,067), copolymers of acrylic acid and maleic anhydride with a molecular mass of the order of 5000 to 75000 (EP-A-0 066 915);

polyethylene glycols with a molecular mass of the order of 1000 to 50000.

EXAMPLES

Concrete but non-limiting examples of the invention are presented below.

Example 1

The subject of this example is the deposition of a cationic-neutral diblock copolymer onto a silica surface measured by In-flow Brewster Angle Reflectometry.

The cationic-neutral diblock copolymer is made up of a polyTMAEAMS (methylsulfate [2-(acryloyloxy)ethyl]-trimethylammonium) first block (Mw=11,000 g/mole) and a polyacrylamide second block (Mw=3,000 g/mole) noted polyTMAEAMS$_{11k}$-b-polyAM$_{3k}$.

1/Synthesis of a Diblock Copolymer PolyTMAEAMS-b-polyAM 11K-3K

The synthesis is carried out according to a batch process, at 70° C., in a double-jacketed reactor.

First Stage: PolyTMAEAMS$_{11k}$-X Synthesis

The solution of [2-(acryloyloxy)ethyl]-trimethylammonium methyl sulfate (TMAEAMS) and water are introduced in the reactor and the solution is heated to 70° C. Then a mixture of S-ethylpropionyl O-ethyl xanthate, 4,4'-azo-bis-4-cyanovaleric acid or ACVA (30 mole % relative to the xanthate) and isopropanol is introduced. The obtained mixture is stirred overnight at 70° C.

| Mass of the reagents introduced per 100 g of final diblock solution | | | | |
|---|---|---|---|---|
| TMAEAMS (80 w % in water) | Water | Xanthate | ACVA | Isopropanol |
| 12.69 g | 16.92 g | 0.20 g | 0.08 g | 3.32 g |

Second Stage: PolyTMAEAMS$_{11k}$-PAM$_{3k}$ Synthesis

The ACVA (50 mole % relative to the xanthate) dissolved in the water is added to the previous mixture.

| Mass of the reagents introduced | |
|---|---|
| ACVA | Water |
| 0.13 g | 49.86 g |

The acrylamide dissolved in the water (I) is then added continuously during 3 hours. After the first hour, the ACVA (22 mole % relative to the xanthate) dissolved in the water (II) is added.

| Mass of the reagents introduced | | | |
|---|---|---|---|
| Acrylamide | Water (I) | ACVA | Water (II) |
| 2.77 g | 7.87 g | 0.06 g | 3.00 g |

After the second hour, the ACVA (22 mole % relative to the xanthate) dissolved in the water is added.

| Mass of the reagents introduced | |
|---|---|
| ACVA | Water |
| 0.06 g | 3.00 g |

After the three hours, the mixture is again stirred at 70° C. for two hours.

The dry extract of the final solution is 13.2%.

Consequently a series of diblock copolymers polyTMAEAMS$_{11k}$-b-polyAM$_{xk}$ with (X=0, 3, 15 and 30) were synthetized according to the protocol described above adapting for each one of them to the adequate quantities of acrylamide, water, initiator and transfer agent.

2/Deposition of Cationic-Neutral Diblock Copolymers onto a Silica Surface Measured by In-Flow Brewster Angle Reflectometry.

The previously obtained diblock copolymers solutions are each brought to neutral pH with Sodium Hydroxide to compensate any slight excess of Methyl Sulfate, and are then diluted with water to obtain a final active level of 5 ppm.

The standardized silica surfaces used were generated by oxidizing silicon wafers, purchased from Wafer World, Inc (Florida, USA) in a 1000° C. furnace. The deposition was then quantified by using a Brewster Angle Reflectometry at the solid-liquid interface at the stagnation point in a flow cell. The reflectometer was built by Prof. Martin Cohen-Stuart's group at Wageningen University in Holland. (see J. C. Dijt, M. A. Cohen Stuart and G. J. Fleer, Advances in Colloid and Interface Science, 50, 1994; 79–101).

As seen in Table 1 Cationic-Neutral copolymers polyTMAEAMS$_{11k}$-b-polyAM$_{xk}$ diblocks copolymers adsorb onto model anionic surfaces of Silica. Most of the adsorbed primary layers do not rinse off with water. The amount remaining depends on the size of the neutral "brush" and is always comprised between 55 to 100%. The minimum desorption is obtained with the smaller "brush".

TABLE 1

Adsorption of polyTMAEAMS$_{11k}$-b-polyAM$_{xk}$ Diblock Copolymers:

| polyTMAEAMS$_{11k}$-b-polyAM$_{xk}$ | Level Absorbed (a.u.) | Level Absorbed after rinsing with water (a.u.) |
|---|---|---|
| 11k0k | 110 | 100 |
| 11k3k | 145 | 135 |
| 11k15k | 510 | 340 |
| 11k30k | 650 | 370 |

Example 2

The subject of this example is the deposition of a secondary layer, that of Sodium Dodecyl Sufate, by complexation onto a primary deposited layer of cationic-neutral diblock copolymer onto a silica surface. The adsorption is measured by In-flow Brewster Angle Reflectometry.

The primary layer is obtained following the protocol described in Example 1. A 200 ppm Sodium Dodecyl Sulfate (SDS, fluka) solution is prepared and introduced into the flow cell of the reflectometer and an adsorption is measured. (See Table 2). 50% of this complexed secondary surfactant layer remains adsorbed by complexation after rinsing with water. Subsequently the 5 ppm solution of polyTMAEAMS$_{11k}$-b-polyAM$_{3k}$ is reintroduced and further adsorption is observed. For this diblock copolymer further adsorption of the 200 ppm solution of SDS did not sustained rinsing and did not remain adsorbed.

TABLE 2

Adsorption of Multilayers in situ complexation of SDS onto polyTMAEAMS$_{11k}$-b-polyAM$_{3k}$ Diblock Copolymers:

| Solution introduced | Level Absorbed (a.u.) | Level Absorbed after rinsing with water (a.u.) |
|---|---|---|
| polyTMAEAMS$_{11k}$-b-polyAM$_{3k}$ 5 ppm | 320 | 310 |
| SDS 200 ppm | 520 | 400 |
| polyTMAEAMS$_{11k}$-b-polyAM$_{3k}$ 5 ppm | 520 | 520 |
| SDS 200 ppm | 620 | 520 |

Example 3

The subject of this example is the deposition of colloidal complexes of cationic-neutral diblock copolymers and Sodium Dodecyl Sulfate onto a silica surface measured by In-flow Brewster Angle Reflectometry.

The cationic-neutral diblock copolymer is made up of a polyTMAEAMS (methylsulfate [2-(acryloyloxy)ethyl]-trimethylammonium) first block (Mw=11,000 g/mole) and a polyacrylamide second block (Mw=30,000 g/mole) noted polyTMAEAMS$_{11k}$-b-polyAM$_{30k}$.

1/Synthesis of a Diblock Copolymer PolyTMAEAMS-b-polyAM 11K-30K

The synthesis is carried out according to a batch process, at 70° C., in a double-jacketed reactor.

First Stage: PolyTMAEAMS$_{11k}$-X Synthesis

The solution of [2-(acryloyloxy)ethyl]-trimethylammonium methyl sulfate (TMAEAMS) and water are introduced in the reactor and the solution is heated to 70° C. Then a mixture of S-ethylpropionyl O-ethyl xanthate, 4,4'-azo-bis-4-cyanovaleric acid or ACVA (30 mole % relative to the xanthate) and isopropanol is introduced. The obtained mixture is stirred overnight at 70° C.

Mass of the reagents introduced per 100 g of final diblock solution

| TMAEAMS (80 w % in water) | Water | Xanthate | ACVA | Isopropanol |
|---|---|---|---|---|
| 6.69 g | 8.92 g | 0.103 g | 0.042 g | 1.75 g |

Second Stage: PolyTMAEAMS$_{11k}$-PAM$_{30k}$ Synthesis

The ACVA (50 mole % relative to the xanthate) dissolved in the water is added to the previous mixture.

Mass of the reagents introduced

| ACVA | Water |
|---|---|
| 0.07 g | 26.28 g |

The acrylamide dissolved in the water (I) is then added continuously during 3 hours. After the first hour, the ACVA (22 mole % relative to the xanthate) dissolved in the water (II) is added.

Mass of the reagents introduced

| Acrylamide | Water (I) | ACVA | Water (II) |
|---|---|---|---|
| 14.6 g | 41.5 g | 0.03 g | 0.05 g |

After the second hour, the ACVA (22 mole % relative to the xanthate) dissolved in the water is added.

Mass of the reagents introduced

| ACVA | Water |
|---|---|
| 0.03 g | 0.05 g |

After the three hours, the mixture is again stirred at 70° C. for two hours.

The dry extract of the final solution is 20%.

2/Formation of Colloidal Complexes

Solution 3A:

The previously obtained diblock copolymer solution is brought to neutral pH with Sodium Hydroxide to compensate any slight excess of Methyl Sulfate, and is then diluted with water to obtain a final active level of 5 wt %.

A series of solutions is prepared by mixing solution 3A with an aqueous 5 wt. % solution of anionic surfactant SDS (Sodium Dodecyl Sulfate, Fluka) in such a way that the molar ratio of the totality of the anionic charges to the totality of the cationic charges, $Z=[-]/[+]$ equals 0.1, 1, 10 and 40. The resulting solutions containing stable light scattering colloids are diluted down with water to a 5 ppm active level.

All these solutions are introduced into the reflectometer and the respective absorption is measured. Each solution represents one adsorption measurement.

TABLE 3

Adsorption of [SDS/polyTMAEAMS$_{11k}$-PAM$_{30k}$] Complexes at varying charge ratio (Z).

| Z of the 5 ppm solution introduced | Level Absorbed (a.u.) | Level Absorbed after rinsing with water (a.u.) |
|---|---|---|
| Z = 0 | 195 | 175 |
| Z = 0.1 | 375 | 260 |
| Z = 1 | 490 | 340 |
| Z = 10 | 560 | 395 |
| Z = 40 | 565 | 360 |

This example shows that a deposition occurs with (Z≠0) or without (Z=0) the surfactant, within a very large range of ingredients and/or charges ratios.

Example 4

The subject of this example is the deposition of colloidal co-complexes of cationic homopolymers, cationic-neutral diblock copolymers and Sodium Dodecyl Sulfate onto a silica surface measured by In-flow Brewster Angle Reflectometry.

The cationic-neutral diblock copolymer is made up of a polyTMAEAMS (methylsulfate [2-(acryloyloxy)ethyl]-trimethylammonium) first block (Mw=11,000 g/mole) and a polyacrylamide second block (Mw=30,000 g/mole) noted polyTMAEAMS$_{11k}$-b-polyAM$_{30k}$.

2/Formation of Colloidal Complexes with Homopolymer

Solution 4A:

The previously obtained diblock copolymer solution is brought to neutral pH with Sodium Hydroxide to compensate any slight excess of Methyl Sulfate, and is then diluted with water to obtain a final active level of 5 wt %.

Solution 4B:

A 5 wt. % solution of [2-(acryloyloxy)ethyl]-trimethylammonium methyl sulfate (TMAEAMS) homopolymer is prepared by diluting a 20 wt. % solution obtained following the same synthesis as described above for the first cationic block (Average Mw=11,000 g/mole). The pH of this solution was also fixed to neutrality.

Series of Solutions 4C:

A series of mixtures of the two solutions 2A and 2B is prepared in order to have 0%, 20%, 35% and 50% of TMAEAMS groups belonging to the Homopolymer.

Series of Solutions 4D:

This resulting mixed 5 wt. % solutions 4C are then further mixed with an aqueous 5 wt. % solution of anionic surfactant SDS (Sodium Dodecyl Sulfate, Fluka) in such a way that the molar ratio of the totality of the anionic charges to the totality of the cationic charges, $Z=[-]/[+]$ equals 1. The resulting solutions containing stable light scattering colloids are diluted down with water to a 10 ppm active level and are then introduced in the flow cell of the reflectometer and the resulting adsorptions measured. Each solution represents an experiment. (See Table 4).

TABLE 4

Adsorption of Co-complexes of [polyTMAEAMS$_{11k}$ homopolymer + polyTMAEAMS$_{11k}$-PAM$_{30k}$ diblock copolymers] with Sodium Dodecyl Sulfate.

| Homopolymer/Diblock | Level Absorbed (a.u.) | Level Absorbed after rinsing with water (a.u.) |
| --- | --- | --- |
| 0/100 | 705 | 410 |
| 20/80 | 485 | 400 |
| 35/65 | 320 | 210 |
| 50/50 | 240 | 195 |

What is claimed is:

1. A method for depositing a polymer onto a hair or skin surface comprising the step of applying a composition comprising said polymer onto the surface, wherein the composition comprises a di-block (block A)–(block B) copolymer (a), comprising two blocks A and B, wherein block A is a polyanionic block and comprises repeating units deriving from monomers selected from the group consisting of:

alpha-ethylenically-unsaturated monomers comprising a phosphate or phosphonate group, alpha-ethylenically-unsaturated monocarboxylic acids, monoalkylesters of alpha-ethylenically-unsaturated dicarboxylic acids, monoalkylamides of alpha-ethylenically-unsaturated dicarboxylic acids, alpha-ethylenically-unsaturated compounds comprising a sulphonic acid group, and salts of alpha-ethylenically-unsaturated compounds comprising a sulphonic acid group, block B is a neutral block in the pH conditions of the formulation, and block A and block B comprise units deriving from a mono-alpha-ethylenically-unsaturated monomer.

2. A method according to claim 1, wherein block A and block B are water-soluble blocks.

3. A method according to claim 1, wherein the composition further comprises a surfactant (b).

4. A method according to claim 3, wherein surfactant (b) is a cationic surfactant in the pH conditions of the composition.

5. A method according to claim 4, wherein surfactant (b) and block copolymer (a) form a complex dispersed in water in the composition, said complex being deposited onto the surface.

6. A method according to claim 3, wherein the composition further comprises a polyionic polymer (c), that interacts with the surface, polymer (c) being a polycationic polymer in the pH condition of the composition.

7. A method according to claim 6, wherein surfactant (b) is an anionic surfactant in the pH condition of the composition, polymer (c) is a polycationic polymer in the pH condition of the composition.

8. A method according to claim 7, wherein polymer (c), surfactant (b), and block polymer (a) form a complex dispersed in water in the composition, said complex being deposited onto the surfaces.

9. A method for depositing a polymer onto a hair or skin surface comprising the step of applying a composition comprising said polymer onto the surface, wherein the composition comprises a di-block (block A)–(block B) copolymer (a) comprising two blocks A and B, wherein block A is a polyanionic block and comprises repeating units deriving from monomers selected from the group consisting of:

acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulphonate (SS).

10. A method according to claim 1, wherein block B comprises repeating units deriving from monomers selected from the group consisting of:

polyethylene and/or polypropylene oxide (meth)acrylates vinyl acetate, amides of alpha-ethylenically-unsaturated carboxylic acids, esters of alpha-ethylenically-unsaturated monocarboxylic acids, vinyl nitriles, vinylamine amides vinyl alcohol vinyl pyrrolidone, and vinyl aromatic compounds.

11. A method according to claim 1, wherein block B comprises repeating units deriving from monomers selected from the group consisting of:

styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate and 2-hydroxyethylacrylate.

12. A method according to claim 2, wherein block B is a hydrophilic water-soluble block and comprises units deriving from monomers selected from the group consisting of:
- vinyl alcohol,
- vinyl pyrrolidone,
- polyethylene oxide (meth)acrylate (i.e. polyethoxylated (meth)acrylic acid),
- hydroxyalkylesters of alpha-ethylenically-unsaturated, monocarboxylic acids,
- hydroxyalkylamides of alpha-ethylenically-unsaturated monocarboxylic acids,
- acrylamide, and methacrylamide.

13. A method according to claim 1, wherein block copolymer (a) is obtained by a living or controlled free-radical polymerization process.

14. A method according to claim 1, wherein the surface is hair surface, and the composition is a hair-conditioning composition.

* * * * *